(12) United States Patent
Shinohara et al.

(10) Patent No.: US 6,923,797 B2
(45) Date of Patent: Aug. 2, 2005

(54) DISPOSABLE UNDERGARMENT

(75) Inventors: Junji Shinohara, Kagawa-ken (JP); Hidefumi Goda, Kagawa-ken (JP); Hirotomo Mukai, Kagawa-ken (JP)

(73) Assignee: Uni-Charm Corporation, Kawanoe (JP)

( * ) Notice: Subject to any disclaimer, the term of this patent is extended or adjusted under 35 U.S.C. 154(b) by 173 days.

(21) Appl. No.: 09/990,262

(22) Filed: Nov. 23, 2001

(65) Prior Publication Data

US 2002/0072728 A1 Jun. 13, 2002

(30) Foreign Application Priority Data

Nov. 24, 2000 (JP) ........................................ 2000-357937

(51) Int. Cl.$^7$ ............................ A61F 13/15; A61F 13/20
(52) U.S. Cl. ............................ 604/385.27; 604/385.29; 604/385.22; 604/385.01
(58) Field of Search ............ 604/385.25, 385.28–385.3, 604/385.22, 385.24, 385.26, 385.27, 385.01, 385.23

(56) References Cited

U.S. PATENT DOCUMENTS

| | | | | |
|---|---|---|---|---|
| 4,685,915 | A | * | 8/1987 | Hasse et al. ................. 604/378 |
| 5,188,627 | A | * | 2/1993 | Igaue et al. ............. 604/385.27 |
| 5,447,508 | A | | 9/1995 | Numano et al. |
| 6,013,065 | A | * | 1/2000 | Suzuki et al. .......... 604/385.27 |
| 6,049,916 | A | * | 4/2000 | Rajala et al. .................... 2/400 |
| 6,210,386 | B1 | * | 4/2001 | Inoue .................... 604/385.13 |
| 6,367,089 | B2 | * | 4/2002 | Van Gompel et al. .......... 2/406 |
| 6,464,677 | B1 | * | 10/2002 | Noguchi et al. ....... 604/385.27 |
| 2002/0045879 | A1 | * | 4/2002 | Karami ....................... 604/391 |
| 2003/0093055 | A1 | * | 5/2003 | Elfstrom et al. ........ 604/385.25 |

FOREIGN PATENT DOCUMENTS

| | | | |
|---|---|---|---|
| EP | 0 990 434 | 4/2000 | |
| EP | 1027874 A2 | * 8/2000 | ......... A61F/13/496 |
| JP | 8-24291 | 1/1996 | |
| WO | WO 93 17648 | 9/1993 | |
| WO | WO 9717920 A1 | * 5/1997 | ........... A61F/13/15 |

OTHER PUBLICATIONS

U.S. Appl. No. 60/330777 and English translation thereof .*
Patent Abstracts of Japan vol. 2000, No. 20, Jul. 10, 2001 097036 A (Uni–Charm Corp) Mar. 27, 2001.
Patent Abstracts of Japan vol. 2000, No. 03, Mar. 20, 2000 & JP 11 332911 (Daio Paper Corp; Daioo Paper Converting KK) Dec. 7, 1999.
Patent Abstracts of Japan vol. 1998 No. 10, Aug. 1998 (Daio Paper Corp)May 19, 1998.

* cited by examiner

*Primary Examiner*—Karin Reichle
(74) *Attorney, Agent, or Firm*—Lowe Hauptman & Berner, LLP (57) ABSTRACT

A disposable undergarment having a topsheet, a backsheet and an absorbent core disposed therebetween. The core is placed in a crotch region and has front and rear end zones and a middle zone. Side portions of a first elastic member extend in the vicinity of front ends of transversely opposite side edge portions of the crotch region while a middle portion of the first elastic member extends across the front end zone. Side portions of a second elastic member extend in the vicinity of rear ends of the edge portions while a middle portion of the second elastic member extends across the rear end zone. The contraction of the first and second elastic members in the middle portions thereof is effectively used to maintain the front and rear end zones of a core in close contact with the wearer's skin.

25 Claims, 8 Drawing Sheets

DISPOSABLE UNDERGARMENT

BACKGROUND OF THE INVENTION

This invention relates to disposable undergarments for absorption and containment of excretion and more particularly, to disposable undergarments such as diapers, training pants, incontinence pants or the like.

Japanese Patent Application Publication No. 1996-24291A describes a disposable pull-on diaper comprising a liquid-pervious topsheet, a liquid-impervious backsheet and a liquid-absorbent core disposed between these two sheets so as to configure a front waist region, a rear waist region and a crotch region extending between these two waist regions. The front and rear waist regions are connected to each other along transversely opposite side edge portions of these front and rear waist regions to define a waist-opening and a pair of leg-openings.

The known diaper is constructed as follows: A stretchable first elastic member is attached under tension to the diaper so as to extend in a circular arc from front ends of transversely opposite side edge portions of the diaper toward a longitudinally middle zone of the crotch region and a stretchable second elastic member is attached under tension to the diaper so as to extend in a circular arc from rear ends of the transversely opposite side edge portions of the diaper toward the longitudinally middle zone of the crotch region. The first and second elastic members respectively comprise both side portions extending in the vicinity of the front and rear ends of the transversely opposite side edge portions of the diaper and middle portions opposed to and spaced apart from each other in the longitudinal direction and extending across the longitudinally middle zone of the crotch region. A pair of stretchable third elastic members are attached under tension to the diaper along the transversely opposite side edge portions thereof so as to extend in the longitudinal direction between the respective middle portions of the first and second elastic members. The transversely opposite side edge portions define peripheral edge portions of respective leg-openings.

With this diaper put on the wearer, the thighs are fully and tightly surrounded by the both side portions of the first and second elastic members and the third elastic members although the first and second elastic members are spaced apart from each other in longitudinal direction in the crotch region, so there is no anxiety that leakage of excretion might occur in the crotch region.

However, desired contraction of the first and second elastic members in the middle portions thereof may be obstructed by the core having a stiffness higher than the top- and backsheets. Insufficient contraction of the middle portions makes it difficult to press a zone of the core against the wearer's skin since a good fit of the core to the wearer's skin relies on the contraction of the middle portions. Certainly it will be possible for the known diaper to press a middle zone of the core against the wearer's skin since the respective middle portions of the first and second elastic members extend across the longitudinally middle zone of the crotch region even if the contraction of the respective middle portions is insufficient. However, it is impossible for the known diaper to press the front and rear end zones of the core against the wearer's skin.

SUMMARY OF THE INVENTION

It is an object of this invention to provide a disposable undergarment improved so that the contraction of the first and second elastic members in the middle portions thereof can be effectively used to press the front and rear zones of the core against the wearer's skin.

According to this invention, there is provided a disposable undergarment comprising a liquid-pervious topsheet, a liquid-impervious backsheet and a liquid-absorbent core disposed between these two sheets so as to configure a front waist region, a rear waist region and a crotch region extending between these two waist regions. The crotch region is formed along parts of both side edge portions thereof with transversely opposite side edge portions curving inward transversely of the diaper and defines peripheral edge portions of leg-openings. The undergarments are provided with a stretchable first elastic member attached under tension thereto so as to extend in a circular arc from a vicinity of front ends of the transversely opposite side edge portions toward a longitudinally middle zone of the crotch region. A stretchable second elastic member is attached under tension thereto so as to extend in a circular arc from a vicinity of rear ends of the transversely opposite side edge portions toward the longitudinally middle zone of the crotch region.

The undergarment further comprises the core being placed substantially in the crotch region and including a middle zone extending in the longitudinally middle zone of the crotch region, a front end zone extending from the middle zone toward the front waist region and a rear end zone extending from the middle zone toward the rear waist region. The first elastic member includes first side portions extending in the vicinity of the front ends of the transversely opposite side edge portions and a first middle portion and the first middle portion extending, on the side facing the backsheet, across the front end zone of the core. The second elastic member includes second side portions extending in the vicinity of the rear ends of the transversely opposite side edge portions and a second middle portion extending, on the side facing the backsheet, across the rear end zone of the core.

According to one preferred embodiment of this invention, stiffness of the core is lower in the front and rear end zones than in the middle zone.

According to another preferred embodiment of this invention, between the first middle portion of the first elastic element and the second middle portion of the second elastic member, third elastic members are attached under tension to the undergarment so as to extend in the longitudinal direction along the transversely opposite side edge portions.

DETAILED DESCRIPTION OF THE PREFERRED EMBODIMENTS

Details of a disposable diaper as an embodiment of this invention will be more fully understood from the description given hereunder with reference to the accompanying drawings.

Figure 1:
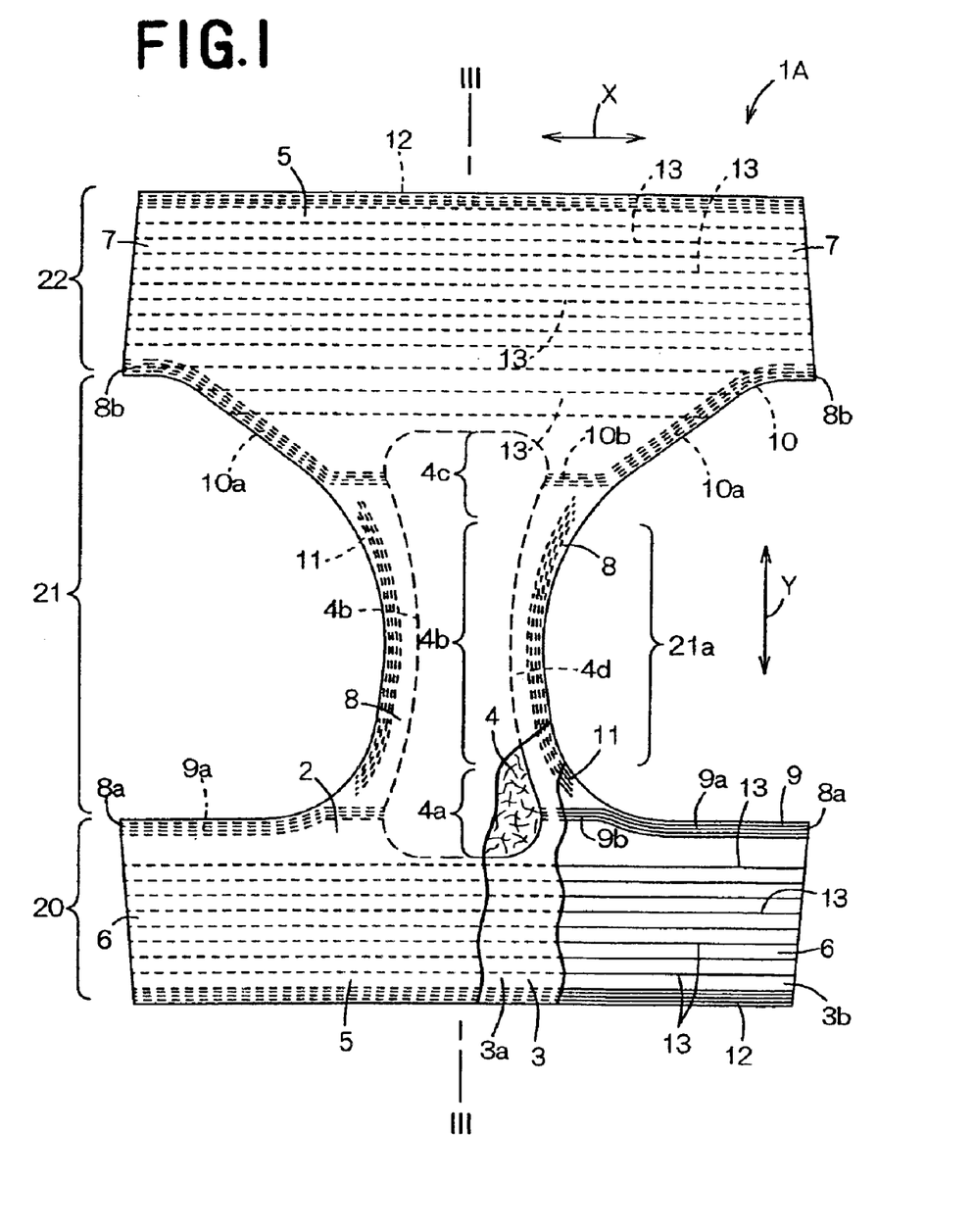
FIG. 1 is a partially cutaway plan view showing a diaper before it is shaped into pants.
Figure 2:
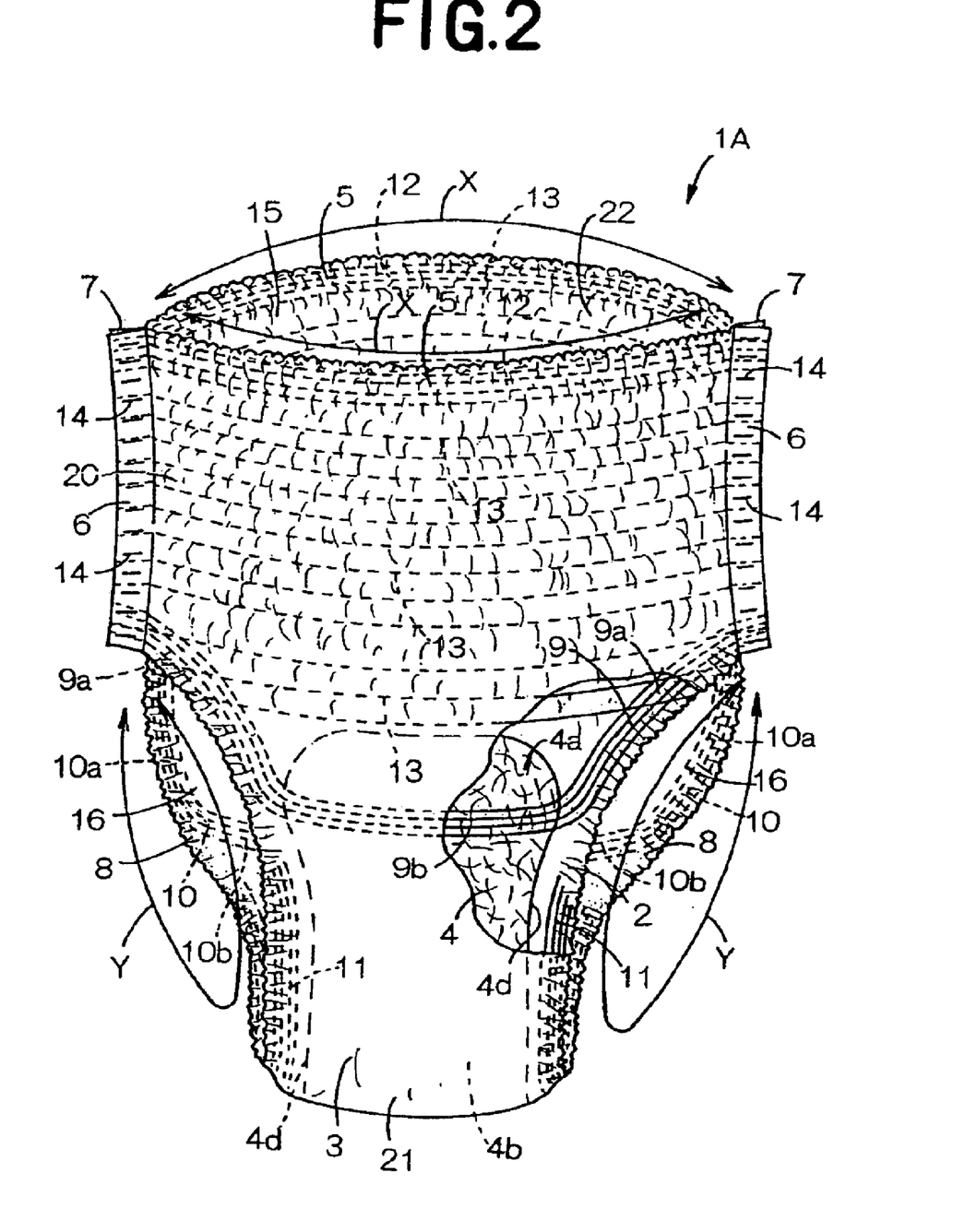
FIG. 2 is a partially cutaway plan view showing the diaper shaped from the state of FIG. 1 into pants.
Figure 3:
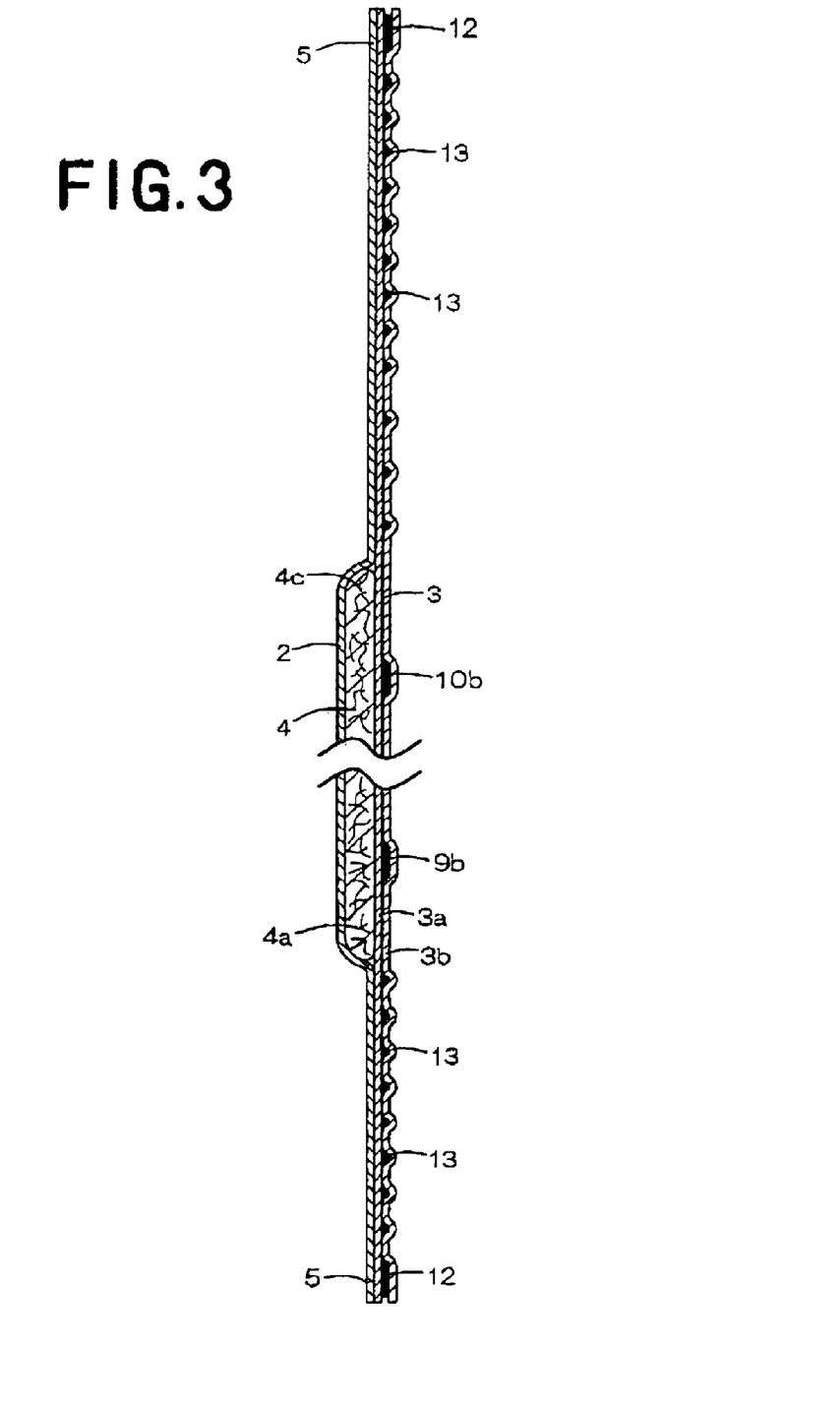
FIG. 3 is a sectional view taken along a line III—III in FIG. 1 with a middle zone of an absorbent core eliminated.

FIG. 1 is a partially cutaway plan view showing a diaper 1A before it is shaped into pants. FIG. 2 is a partially cutaway perspective view showing the diaper 1A having been shaped into pants from the state of FIG. 1 and FIG. 3 is a sectional view taken along a line III—III in FIG. 1. In FIG.1, a transverse direction is indicated by an arrow X and a longitudinal direction is indicated by an arrow Y. In FIG. 2, a waist-surrounding direction is indicated by an arrow X and a leg-surrounding direction is indicated by an arrow Y. Surfaces of the top- and backsheets 2, 3 facing an absorbent core 4 will be referred to herein as inner surfaces thereof and surfaces of these sheets 2, 3 not facing the absorbent core 4 will be referred to herein as outer surfaces thereof.

The diaper 1A basically comprises a liquid-pervious topsheet 2, a liquid-impervious backsheet 3 formed of a composite sheet composed of a plastic film 3b joined to a hydrophobic fibrous nonwoven fabric 3a and a liquid-absorbent core 4 disposed between the top- and backsheets 2, 3 and joined to the inner surfaces of these sheets 2, 3.

As will be apparent from FIG. 1, the diaper 1A has, in the longitudinal direction, a front waist region 20, a rear waist region 22 and a crotch region 21 extending between these waist regions 20, 22. The diaper is 1A is defined by longitudinally opposite end portions 5 transversely extending in the front and rear waist regions 20, 22 and transversely opposite side edge portions 6, 7 longitudinally extending in the front and rear waist regions 20, 22.

The crotch region 21 is formed along its transversely opposite side edges with cutouts respectively curving inward transversely to define peripheral edge portions 8 of a pair of leg-openings. The crotch region 21 is provided with elastically stretchable first elastic member 9, a second elastic member 10 and a third elastic member 11, each comprising a plurality of elastic elements and attached under tension to the crotch region 21.

The absorbent core 4 is placed in the crotch region 21 and extends in the longitudinal direction. The core 4 has a middle zone 4b extending across a longitudinally middle zone 21a of the crotch region 21, a front end zone 4a extending from the middle zone 21a toward the front waist region 20 and a rear end zone 4c extending from the middle zone 21a toward the rear waist region 22. The front end zone 4a of the core 4 extends slightly into the front waist region 20. Transversely opposite side edges 4d of the core 4 extending in the longitudinal direction inside the transversely opposite side edge portions 8 of the crotch region 21 curve inward transversely of the diaper 1A so as to describe circular arcs.

The core 4 is formed of a mixture of fluff pulp fibers and high absorption polymer particles or a mixture of fluff pulp fibers, high absorption polymer particles and thermoplastic synthetic resin fibers compressed to a desired thickness. Therefore, the core 4 has stiffness or rigidity (hereinafter referred to as stiffness) higher than that of the top- and backsheets 2, 3.

Figure 8:
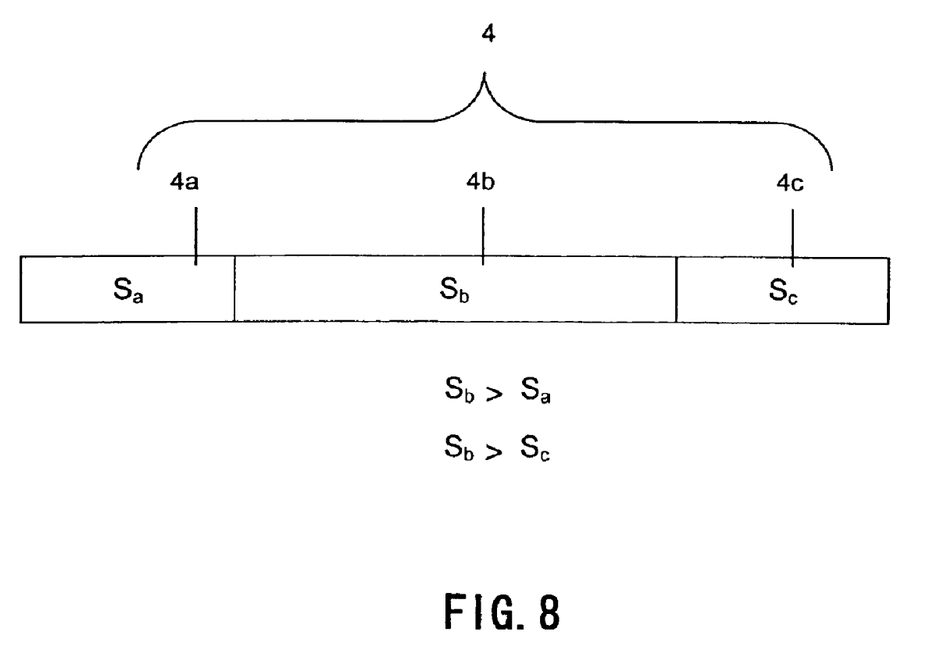
FIG. 8 is a view schematically showing the stiffness of the core in various regions thereof.

Regarding the core 4, the front and rear end zones 4a, 4c have stiffness ($S_a$ and $S_c$, respectively) lower than that of the middle zone 4b ($S_b$, as can be seen in FIG. 8). To ensure that the front and rear end zones 4a, 4c have such stiffness lower than that of the middle zone 4b, for example, the basis weight of the core 4 in the front and rear end zones 4a, 4c may be adjusted to be lower than that of the core 4 in the middle zone 4b, provided that the thicknesses of the core 4 in all the zones 4a, 4b and 4c are uniform. That is, the density of the core 4 in the front and rear end zones 4a, 4c may be adjusted to be lower than that of the core 4 in the middle zone 4b.

The first elastic member 9 extends from respective front ends 8a of the transversely opposite side edge portions 8 lying in the front waist region 20 toward the longitudinally middle zone 21a of the crotch region 21 substantially so as to describe circular arcs. The first elastic member 9 comprises both side portions 9a extending along the transversely opposite side edges 8 in the vicinity of the front ends 8a thereof and a middle portion 9b extending across the front end zone 4a of the core 4.

The second elastic member 10 extends from respective rear ends 8b of the transversely opposite side edge portions 8 lying in the rear waist region 22 toward the longitudinally middle zone 21a of the crotch region 21 substantially so as to describe circular arcs. The second elastic member 10 comprises both side portions 10a extending along the transversely opposite side edges 8 in the vicinity of the rear ends 8b thereof and a middle portion 10b extending across the rear end zone 4c of the core 4.

The third elastic members 11 extend along the transversely opposite side edges 8 in the longitudinal direction outside the respective side edges 4d of the core 4 between the middle portion 9b of the first elastic member 9 and the middle portion 10b of the second elastic member 10. The first, second and third elastic members 9, 10, 11 are disposed between the fibrous nonwoven fabric 3a and the plastic film 3b forming together the backsheet 3 and secured to them.

Transversely extending elastic members 12 associated with a waist-opening each comprising a plurality of elastic elements are attached under tension to the longitudinally opposite end portions 5 of the diaper. Between the respective elastic members 12 associated with the waist-opening, on one hand, and the first and second elastic members 9, 10, on the other hand, an auxiliary elastic member 13 comprising a plurality of elastic elements is attached under tension so as to extend in the transverse direction across the front and rear waist regions 20, 22. The elastic members 12 and the auxiliary elastic member 13 are disposed between the fibrous nonwoven fabric 3a and the plastic film 3b and secured thereto.

As shown in FIG. 2, the front and rear waist regions 20, 22 are joined to each other along transversely opposite side edge portions 6, 7 of the waist regions 20, 22 by means of joining zones 14 arranged intermittently in the longitudinal direction to shape the diaper 1A into pants. A waist-opening 15 and a pair of leg-openings 16 are defined as the diaper 1A is shaped in this manner. With regard to the diaper 1A, the longitudinally opposite end portions 5 define a peripheral edge portion of the waist-opening 15 and the transversely opposite side edge portions 8 define peripheral edge portions of the respective leg-openings 16.

Both side portions 9a, 10a of the first and second elastic members 9, 10 and the third elastic member 11 extend in a leg-surrounding direction along the peripheral edge portions of the leg-openings 16. The elastic member 12 associated with the waist-opening extends in a waist-surrounding direction along the peripheral edge portion of the waist-opening 15. The auxiliary elastic member 13 extends in the waist-surrounding direction across the front and rear waist regions 20, 22. In the diaper 1A, a plurality of gathers are formed along the peripheral edge portions of the waist- and leg-openings 15, 16 as well as in the front and rear waist regions 20, 22 as the elastic members 9, 10, 11, 12, 13 contract.

Figure 4:
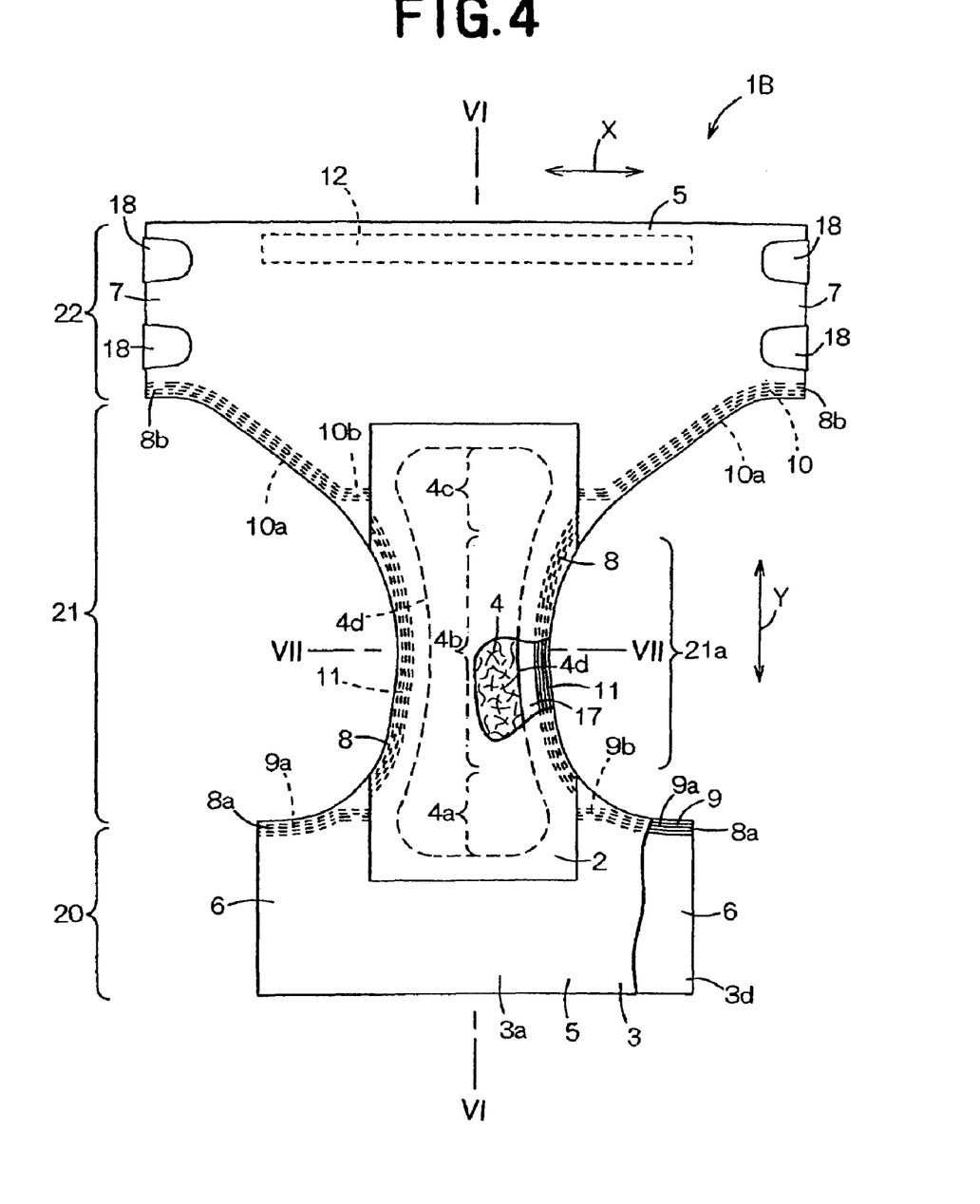
FIG. 4 is a partially cutaway plan view showing open-type diaper.
Figure 5:
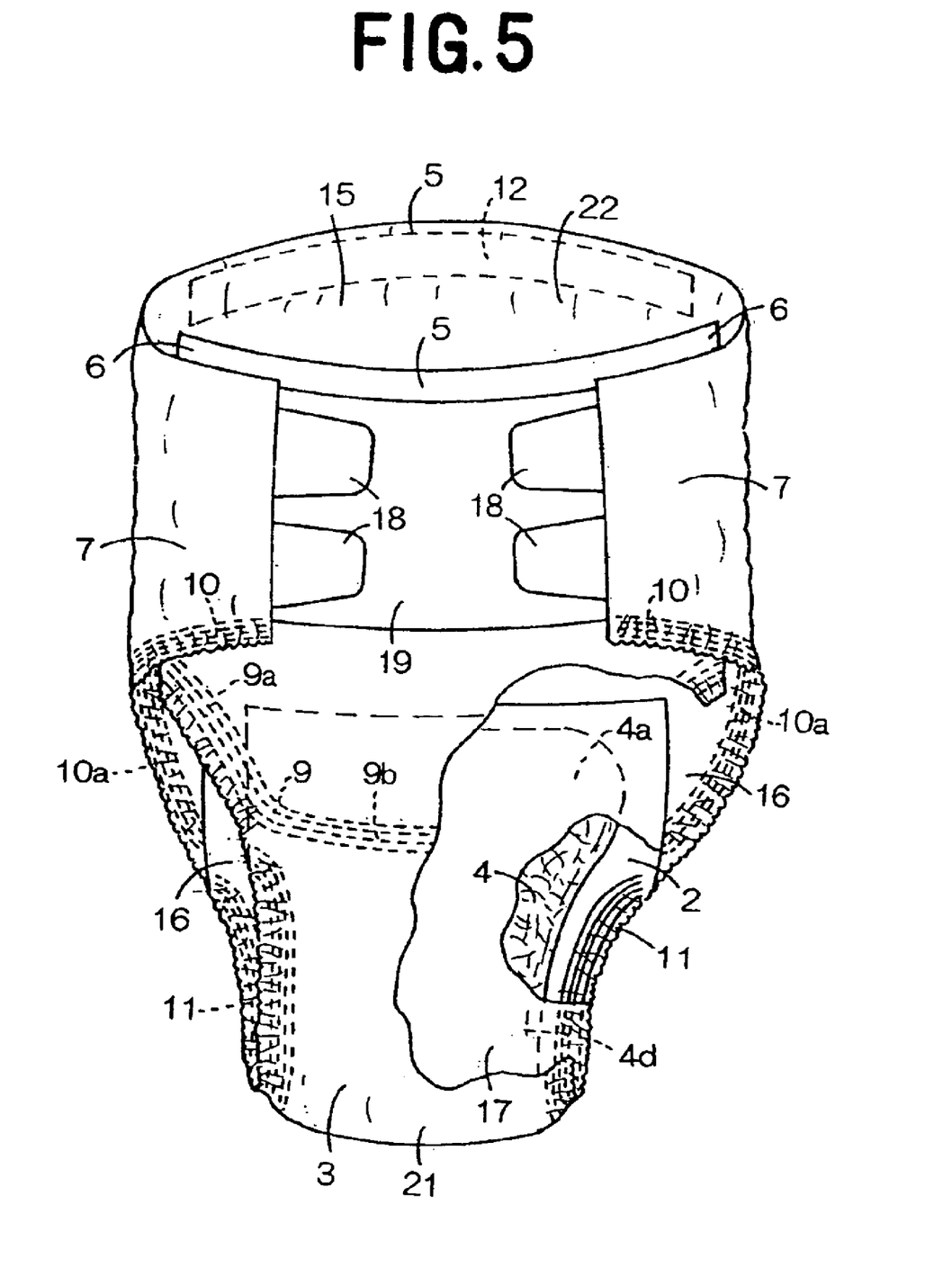
FIG. 5 is a perspective view showing the diaper with front and rear waist regions connected together for wearing.
Figure 6:
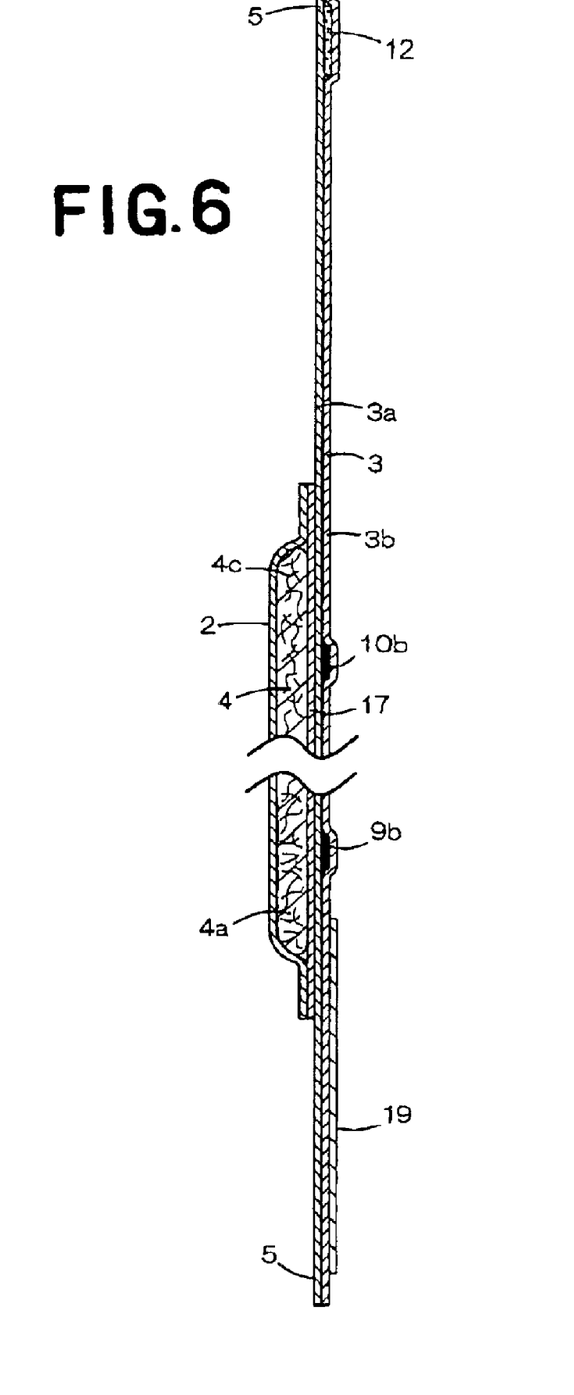
FIG. 6 is a sectional view taken along a line VI—VI in FIG. 4 with the middle zone of the core eliminated.
Figure 7:
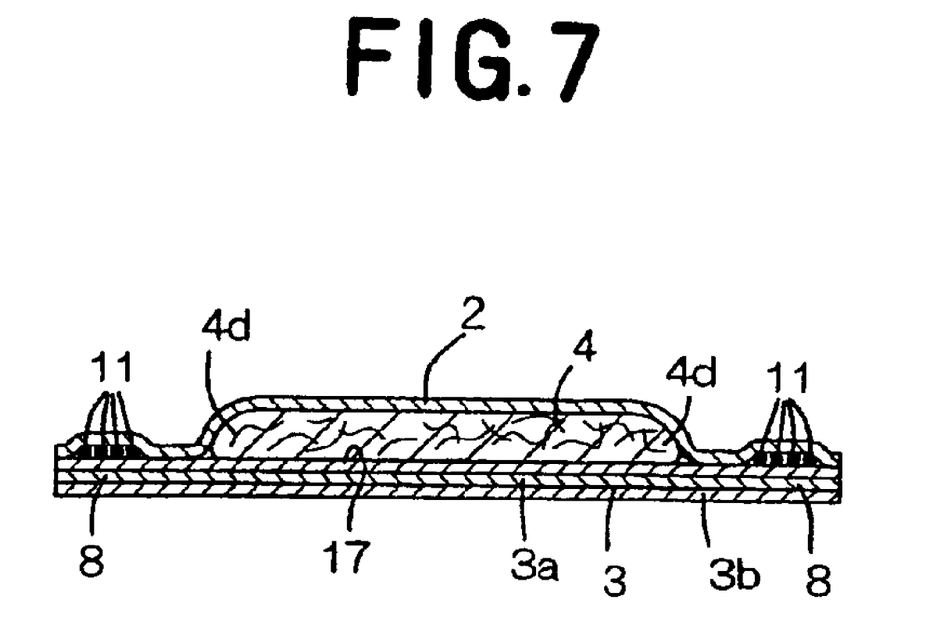
FIG. 7 is a sectional view taken along a line VII—VII in FIG. 4.

FIG. 4 is a partially cutaway plan view showing an open-type diaper 1B, FIG. 5 is a partially cutaway perspective view showing the diaper 1B with the front and rear waist regions 20, 22 connected to each other to be ready for wearing, and FIGS. 6 and 7 are sectional views taken along lines VI—VI and VII—VII, respectively, and in FIG. 6 with the middle zone 4b of the core 4 being eliminated. In FIG. 4, a transverse direction is indicated by an arrow X and a longitudinal direction is indicated by an arrow Y. In FIG. 5, the waist-surrounding direction is indicated by an arrow X and the leg-surrounding direction is indicated by an arrow Y.

The diaper 1B basically comprises a liquid-pervious topsheet 2, a liquid-impervious leak-barrier sheet 17, a liquid-absorbent core 4 disposed between these sheets 2, 17 and entirely covered with tissue paper (not shown) and joined thereto, and a liquid-impervious backsheet 3 composed of a hydrophobic fibrous nonwoven fabric 3a and a plastic film 3b bonded to the fibrous nonwoven fabric 3a. The backsheet 3 presents an hourglass-shape peculiar to the open-type diaper which defines front and rear waist regions 20, 22 and a crotch region 21 of the diaper 1B.

The core 4 is placed in the crotch region 21 and comprises front and rear end zones 4a, 4c and a middle zone 4b. The front and rear end zones 4a, 4c of the core 4 have a stiffness lower than that of the middle zone 4b. The core 4 is joined to inner surfaces of the topsheet 2 and the leak-barrier sheet 17 with the tissue paper therebetween.

Peripheral portions of the topsheet 2 and the leak-barrier sheet 17 extend outward slightly beyond the peripheral edge of the core 4 and put flat and joined together. The leak-barrier sheet 17 is joined to the inner surface of the backsheet 3 in the crotch region 21.

Transversely opposite side edge portions of the crotch region 21 partially define transversely opposite side edge portions 8 curving inward transversely of the diaper 1B so that the portions 8 are destined to define the peripheral edge portions of respective leg-openings. The crotch region 21 is provided with a first elastic member 9 extending in circular arc from front ends 8a of the transversely opposite side edge portions 8 toward a middle zone 21a of the crotch region 21 and a second elastic member 10 extending in circular arc from rear ends 8b of the transversely opposite side edge portions 8 toward the middle zone 21a of the crotch region 21, both of these elastic members 9, 10 being attached under tension to the crotch region 21.

The first and second elastic members 9, 10 respectively comprise both side portions 9a, 10a extending along the transversely opposite side edge portions 8 in the vicinity of the front and rear ends 8a, 8b thereof and middle portions 9b, 10b extending across the front and rear end zones 4a, 4c of the core 4. The first and second elastic members 9, 10 are disposed between the fibrous nonwoven fabric 3a and the plastic film 3b and secured to them.

Between the middle portions 9b, 10b of the first and second elastic members 9, 10, respectively, third elastic members 11 are attached under tension to the crotch region 21. The third elastic members 11 extend in the longitudinal direction along the transversely opposite side edge portions 8 outside the transversely opposite side edges 4d of the core 4. These third elastic members 11 are disposed between the topsheet 2 and the leak-barrier sheet 17 and bonded to them.

A ribbon-like elastic member 12 associated with the waist-opening is attached under tension to the rear waist region 22 along its longitudinal end portion 5. The elastic member 12 associated with the waist-opening is disposed between the fibrous nonwoven fabric 3a and the plastic film 3b and secured to them.

The transversely opposite side edge portions 7 of the rear waist region 22 are provided with a pair of tape fasteners 18 extending inward in the transverse direction. The tape fasteners 18 respectively have proximal end portions disposed between the fibrous nonwoven fabric 3a and the plastic film 3b and joined to them. Free end portions of the respective tape fasteners 18 are coated with pressure-sensitive adhesive (not shown). The front waist region 20 is provided on the outer surface of the backsheet 3 with a rectangular target tape strip 19 made of a plastic sheet. This rectangular target tape strip 19 serves as a landing zone for the tape fasteners 18.

To wear the diaper 1B, the transversely opposite side edge portions 7 of the rear waist region 22 are placed upon outer sides of the transversely opposite side edge portions 6 of the front waist region 20 and the free end portions of the tape fasteners 18 are anchored to the target tape strip 19 by means of pressure-sensitive adhesive 15 to connect the front waist region 20 with the rear waist region 22.

In the diaper 1A as well as in the diaper 1B as have been illustrated and described above, the core 4 has a stiffness lower in its front and rear zones 4a, 4c than in its middle zone 4b, so it is not likely that the contraction of the first and second elastic members 9, 10 might be obstructed by the front and rear end zones 4a, 4c of the core 4. In both diapers 1A, 1B, the front and rear end zones 4a, 4c of the core 4 are tightly pressed against the wearer's skin as the middle portions 9b, 10b contract.

In both diapers 1A, 1B when put on the wearer, the both side portions 9a, 10a of the first and second elastic members 9, 10, respectively, cooperate with the third elastic members 11 to surround the wearer's thighs thereby to seal the full circumferences of the respective thighs of the wearer. In this way, leakage of excretion possibly occurring in the crotch region 21 is reliably avoided although the middle portions 9b, 10b of the first and second elastic members 9, 10 are spaced apart from each other in the longitudinal direction.

In these diapers 1A, 1B, the tensile stress of the both side portions 9a, 10a of the first and second elastic members 9, 10 preferably is greater than that of the middle portions 9b, 10b of the first and second elastic members 9, 10. With the diapers 1A, 1B in which those portions 9a, 10a, 9b, 10b present the tensile stress as represented by the above-described relationship, the contractile force of the both side portions 9a, 10a can sufficiently seal the circumferences of the wearer's thighs and there is no possibility that the front and rear end zones 4a, 4c of the core 4 might be formed with a plurality of gathers even when the middle portions 9b, 10b contract.

The topsheet 2 may be formed of a hydrophilic fibrous nonwoven fabric or a porous plastic film. The leak-barrier sheet 17 may be formed of a liquid-impervious plastic film.

The backsheet 3 may be formed of materials other than the composite sheet composed of the hydrophobic fibrous nonwoven fabric 3a and the plastic film 3b joined to the hydrophobic fibrous nonwoven fabric 3a. In addition to such composite sheet, stock material selected from a group including a hydrophobic fibrous nonwoven fabric, a liquid-impervious plastic film and laminated two layers of a hydrophobic fibrous nonwoven fabric may be used. It is also possible to form the backsheet 3 of a composite nonwoven fabric composed of a melt blown fibrous nonwoven fabric having high water-resistance and two layers of a spun bond fibrous nonwoven fabric having high strength and flexibility.

The nonwoven fabric may be selected from a group including spun lace-, needle punch-, melt blown-, thermal bond-, spun bond-, chemical bond- and air through-nonwoven fabrics. The component fiber of the nonwoven fabric may be selected from a group including polyolefin, polyester and polyamide fibers, and polyethylene/ polypropylene or polyethylene/polyester core-sheath-type or side-by-side type conjugated fibers.

The polymer contained in the core 4 may be selected from a group including a starch- and cellulose-based polymer and a synthetic polymer. The first, second and third elastic members 9, 10, 11, the elastic member 12 associated with the waist-opening and the auxiliary elastic member 13 may be made of elastomer such as synthetic or natural rubber.

Bonding of the top- and backsheets 2,3 to each other, fixing of the leak-barrier sheet 17 to the backsheet 3, joining of the core 4 to the top- and backsheets 2, 3 and attachment of the elastic members 9, 10, 11, 12, 13 may be carried out using hot melt adhesive or heat welding technique such as heat-sealing or sonic sealing.

With the disposable undergarment according to this invention, the middle portions of the first and second elastic members extending across the front and rear end zones can properly contract and thereby the front and rear end zones of the core can be pressed against the wearer's skin under such contraction. In this way, the front and rear end zones of the core can be maintained in close contact with the wearer's skin.

In the case of the undergarment according to the preferred embodiment of this invention in which the core has a stiffness lower in its front and rear zones than in its middle zone, the middle portions of the first and second elastic members can properly contract without being affected by the front and rear zones of the core. Therefore, the contraction of the middle portions of these elastic members can be effectively used to maintain the front and rear zones of the core in close contact with the wearer's skin.

In the case of the undergarment according to the other preferred embodiment of this invention in which the third elastic members extend between the middle portions of the first and second elastic member, respectively, both side portions of the first and second elastic members cooperate with the third elastic members to surround the wearer's thighs and thereby seal the full circumferences of the wearer's thighs. Such a unique arrangement ensures that possible leakage of excretion occurring in the crotch region can be reliably avoided although the middle portions of the first and second elastic members are spaced from each other in the longitudinal direction of the diaper.

What is claimed is:

1. A disposable undergarment, comprising:
   a liquid-pervious topsheet, a liquid-impervious backsheet and a liquid-absorbent core disposed between the topsheet and backsheet;
   a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;
   said core including a front end zone, a rear end zone, and a middle zone extending longitudinally of said undergarment between the front and rear end zones, said middle zone being completely located in said crotch region, said front end zone extending from said middle zone toward said front waist region, and said rear end zone extending from said middle zone toward said rear waist region;
   a first elastic member extending transversely of said undergarment, along a front end portion of one of said transversely opposite side edges of said crotch region, across said front end zone of said core, and along a front end portion of the other of said transversely opposite side edges of said crotch region;
   a second elastic member extending transversely of said undergarment, along a rear end portion of one of said transversely opposite side edges of said crotch region, across said rear end zone of said core, and along a rear end portion of the other of said transversely opposite side edges of said crotch region;
   wherein
   a stiffness of said core is lower in the front and rear end zones than in the middle zone;
   said first elastic member has a central portion underlying said front end zone of said core and being attached under tension to said backsheet; and
   said first elastic member further has end portions on opposite sides of said central portion, each of the end portions of said first elastic member extending along the front end portion of one of said transversely opposite side edges of said crotch region, a tensile stress of said first elastic member being greater in the end portions than in the central portion.

2. The undergarment according to claim 1, wherein the stiffness of said core in the entire front and rear end zones is lower than in the entire middle zone.

3. A disposable undergarment, comprising:
   a liquid-pervious topsheet, a liquid-impervious backsheet and a liquid-absorbent core disposed between the topsheet and backsheet;
   a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;
   said core including a front end zone, a rear end zone, and a middle zone extending longitudinally of said undergarment between the front and rear end zones, said middle zone being completely located in said crotch region, said front end zone extending from said middle zone toward said front waist region, and said rear end zone extending from said middle zone toward said rear waist region;
   a first elastic member extending transversely of said undergarment, along a front end portion of one of said transversely opposite side edges of said crotch region, across said front end zone of said core, and along a front end portion of the other of said transversely opposite side edges of said crotch region;
   a second elastic member extending transversely of said undergarment, along a rear end portion of one of said transversely opposite side edges of said crotch region, across said rear end zone of said core, and along a rear end portion of the other of said transversely opposite side edges of said crotch region;
   wherein
   a stiffness of said core is lower in the front and rear end zones than in the middle zone;
   said second elastic member has a central portion underlying said rear end zone of said core and being attached under tension to said backsheet; and
   said second elastic member further has end portions on opposite sides of said central portion, each of the end portions of said second elastic member extending along the rear end portion of one of said transversely opposite side edges of said crotch region, a tensile stress of said second elastic member being greater in the end portions than in the central portion.

4. The undergarment according to claim 3, further comprising third elastic members attached under tension to said undergarment, each of said third elastic members extending longitudinally of said undergarment, between said first and second elastic members, and along one of said transversely opposite side edges of said crotch region.

5. The undergarment according to claim 4, wherein each of the third elastic members extends between, without contacting or crossing, the first and second elastic members.

6. The undergarment according to claim 4, wherein an entire area of said topsheet is smaller than that of said backsheet and greater than an entire area of an upper surface of said core.

7. The undergarment according to claim 4, wherein said crotch region has a linear area extending perpendicular to a longitudinal direction of said undergarment and continuously from one of the transversely opposite side edges to the other of the transversely opposite side edges, said area being free of said first, second, and third elastic members.

8. The undergarment according to claim 4, wherein said backsheet has at least two material layers including an upper layer and a lower layer, said first and second elastic members are sandwiched between said upper and lower layers, and said third elastic members are sandwiched between said upper layer and said topsheet.

9. The undergarment according to claim 3, wherein said first and second elastic members are not directly attached to the topsheet.

10. The undergarment according to claim 3, wherein the first and second elastic members are spaced apart in a longitudinal direction of said undergarment without contacting or crossing each other.

11. The undergarment according to claim 10, wherein a closest distance between said first and second elastic members as measured in said longitudinal direction is greater than a half of an entire extent of said core as measured in said longitudinal direction.

12. The undergarment according to claim 3, wherein a density of said core is lower in the front and rear end zones than in the middle zone.

13. The undergarment according to claim 3, wherein a basis weight of said core is lower in the front and rear end zones than in the middle zone.

14. The undergarment according to claim 3, wherein a central portion of said first elastic member underlies said front end zone of said core and is directly attached under tension to said backsheet.

15. The undergarment according to claim 3, wherein the stiffness of said core in an area, which area is of the rear end zone, which area is located immediately above the central portion of said second elastic member, is lower throughout said area than the stiffness of the core in the middle zone.

16. The undergarment according to claim 15, wherein the core has a substantially uniform thickness in said area.

17. The undergarment according to claim 16, wherein the rear end zone of said core also has a substantially uniform thickness from said area to a curved rear edge of said core.

18. A disposable undergarment, comprising:
    a liquid-pervious topsheet, a liquid-impervious backsheet and a liquid-absorbent core disposed between the topsheet and backsheet;
    a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;
    said core including a front end zone, a rear end zone, and a middle zone extending longitudinally of said undergarment between the front and rear end zones, said middle zone being completely located in said crotch region, said front end zone extending from said middle zone toward said front waist region, and said rear end zone extending from said middle zone toward said rear waist region;
    a first elastic member extending transversely of said undergarment, along a front end portion of one of said transversely opposite side edges of said crotch region, across said front end zone of said core, and along a front end portion of the other of said transversely opposite side edges of said crotch region;
    a second elastic member extending transversely of said undergarment, along a rear end portion of one of said transversely opposite side edges of said crotch region, across said rear end zone of said core, and along a rear end portion of the other of said transversely opposite side edges of said crotch region;
    wherein a stiffness of said core is lower in the front and rear end zones than in the middle zone, and each of said first and second elastic members includes:
    a central portion underlying the respective one of said front and rear end zones of said core and being attached under tension to said backsheet; and
    end portions on opposite sides of said central portion, each of the end portions extending along the respective one of said front and rear end portions of one of said transversely opposite side edges of said crotch region, wherein a tensile stress of the end portions is greater than that of the central portion.

19. The undergarment according to claim 18, wherein said core is placed substantially in the crotch section, and the first and second elastic members extend in circular arcs towards the longitudinally middle zone of the crotch region.

20. The undergarment according to claim 19, wherein said middle zone of said core, as measured in a longitudinal direction of said undergarment, is longer than both said front and rear end zones of said core.

21. The undergarment according to claim 19, further comprising, in the front regions, plurality parallel auxiliary elastic members extending in a transverse direction of said undergarment, all of the auxiliary elastic members in the front waist regions being forwardly spaced in a longitudinal direction of said undergarment from the front end zone of said core, and all of the auxiliary elastic members in the rear waist regions being rearwardly spaced in the longitudinal direction from the rear end zone of said core.

22. The undergarment according to claim 19, further comprising, in the front and rear waist regions, a plurality of parallel auxiliary elastic members extending in a transverse direction of said undergarment, wherein none of said auxiliary elastic members underlie said core.

23. The undergarment according to claim 18, wherein said middle zone of said core, as measured in a longitudinal direction of said undergarment, is longer than both said front and rear end zones of said core.

24. The undergarment according to claim 23, further comprising, in the front and rear waist regions, a plurality of parallel auxiliary elastic members extending in a transverse direction of said undergarment, wherein none of said auxiliary elastic members underlie said core.

25. The undergarment according to claim 18, further comprising, in the front and rear waist regions, a plurality of parallel auxiliary elastic members extending in a transverse direction of said undergarment, all of the auxiliary elastic members in the front waist regions being forwardly spaced in a longitudinal direction of said undergarment from the front end zone of said core, and all of the auxiliary elastic members in the rear waist regions being rearwardly spaced in the longitudinal direction from the rear end zone of said core.

* * * * *